(12) United States Patent
Chang

(10) Patent No.: US 8,012,478 B2
(45) Date of Patent: Sep. 6, 2011

(54) USE OF ANTI-IL-20 ANTIBODY FOR TREATING STROKE

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 12/246,691

(22) Filed: Oct. 7, 2008

(65) Prior Publication Data

US 2010/0086549 A1    Apr. 8, 2010

(51) Int. Cl.
*A61K 39/395* (2006.01)
(52) U.S. Cl. .............. 424/133.1; 424/135.1; 424/141.1; 530/351; 530/809
(58) Field of Classification Search .......... None
See application file for complete search history.

(56) References Cited

U.S. PATENT DOCUMENTS

| | | | |
|---|---|---|---|
| 5,605,680 A | 2/1997 | Deflandre et al. | |
| 7,122,632 B2 | 10/2006 | Foster et al. | |
| 7,393,684 B2 * | 7/2008 | Xu et al. | 435/335 |
| 7,435,800 B2 | 10/2008 | Chang | |
| 7,611,705 B2 | 11/2009 | Chang | |
| 2005/0003475 A1 | 1/2005 | Foster et al. | |
| 2005/0136004 A1 | 6/2005 | Xu et al. | |
| 2006/0142550 A1 | 6/2006 | Chang | |
| 2006/0177447 A1 | 8/2006 | Xu | |
| 2006/0269551 A1 | 11/2006 | Thompson et al. | |

OTHER PUBLICATIONS

MayoClinic Website, "Stroke" ("Treatment", and "Treatment and drugs"), accessed Sep. 26, 2009.*
Viles-Gonzalez et al. Atherothrombosis: A widespread disease with unpredictable and life-threatening consequences. Jul. 2004, Eur Heart J. 25(14):1197-207.*
Hsu Y.H. et al., "Function of Interleukin-20 as a proinflammatory molecule in rheumatoid and experimental arthritis", Arthritis and Rheumatism, vol. 54(9), pp. 2722-2733 (Sep. 2006).
Hsieh M.Y. et al., "Interleukin-20 promotes angiogenesis in a direct and indirect manner", Genes and Immunity, vol. 7(3), pp. 234-242 (Apr. 2006).
Wei C.C. et al., "IL-20: Biological functions and clinical implications", Journal of Biomedical Science, vol. 13(5), pp. 601-612 (May 16, 2006).
Sabat R. et al., "IL-19 and IL-20: Two novel cytokines with importance in inflammatory diseases", Expert Opinion on Therapeutic Targets, vol. 11(5), pp. 601-612 (May 2007).
Wei C.C. et al., "Detection of IL-20 and its receptors on psoriatic skin", Clinical Immunology, vol. 117(1), pp. 65-72 (Oct. 2005).
Chen, W-Y. et al. (2009). "IL-20 is Regulated by Hypoxia-inducible Factor and Up-Regulated After Experimental Ischemic Stroke," *Journal of Immunology* 182(8):5003-5012.

* cited by examiner

*Primary Examiner* — Dong Jiang
(74) *Attorney, Agent, or Firm* — Occhiuti Rohlicek & Tsao LLP

(57) ABSTRACT

Treatment of stroke with an antibody specific to IL-20, e.g., monoclonal antibody 7E.

6 Claims, 1 Drawing Sheet

USE OF ANTI-IL-20 ANTIBODY FOR TREATING STROKE

BACKGROUND OF THE INVENTION

Stroke is one of the most common diseases that result in disability or death worldwide. Ischemic/hemorrhagic injury and the subsequent inflammation account for the development and progression of this disease.

IL-20, a member of the IL-10 family, is a proinflammatory cytokine involved in pathogenesis of various inflammation-associated diseases.

SUMMARY OF THE INVENTION

The present invention is based on the unexpected discovery that monoclonal antibody 7E, an anti-IL-20 antibody, reduces infarct areas in rats suffering from ischemic stroke.

Accordingly, this invention features a method of treating stroke by administering to a subject in need of the treatment an effective amount of an IL-20-specific antibody (e.g., an anti-IL-20 antibody 7E). In one example, the anti-IL-20 antibody 7E is an antibody containing the heavy chain and light chain variable regions of mAb 7E, which is produced by a hybridoma cell line deposited with the American Type Culture Collection as Deposit Number PTA-8687. Examples of this antibody include, but are not limited to, mAb 7E, a functional fragment thereof (such as F(ab')$_2$ and Fab), a single-chain antibody, or a chimeric antibody. In another example, the anti-IL-20 antibody 7E is a humanized antibody of mAb 7E.

The term "treating" as used herein refers to the application or administration of a composition including one or more active agents to a subject, who has stroke, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

Also within the scope of this invention is use of an anti-IL-20 antibody for treating stroke or for the manufacture of a medicament for this treatment.

The details of one or more embodiments of the invention are set forth in the description below. Other features or advantages of the present invention will be apparent from the following drawing and detailed description of several embodiments, and also from the appending claims.

BRIEF DESCRIPTION OF THE DRAWINGS

The drawing is first described.

DETAILED DESCRIPTION OF THE INVENTION

Figure 1:
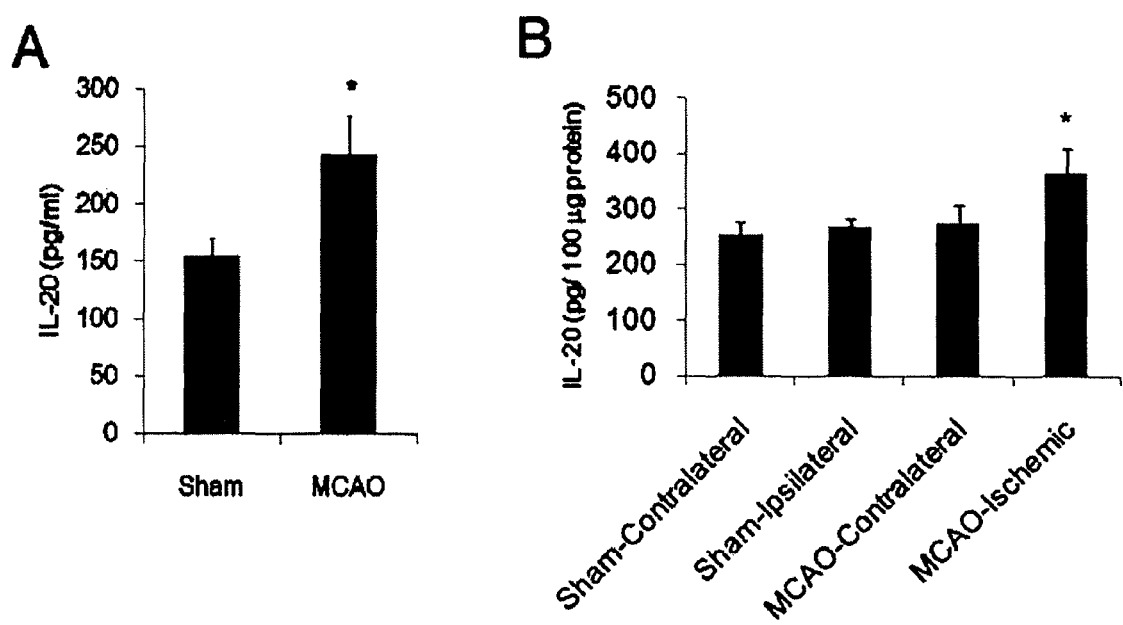
FIG. 1 is charts showing the levels of IL-20 in control mice and mice with occlusion of the right middle cerebral artery (MCAO). Panel A: IL-20 levels in sham control and MCAO mice. Panel B: IL-20 levels in the contralateral/Ipsilateral hemisphere of control mice and in the contralateral/ischemic hemisphere of MCAO mice.

Described herein is a method of treating stroke with an antibody specific to IL-20. The term "antibody" includes intact immunoglobulin molecules, such as monoclonal antibody, polyclonal antibody, chimeric antibody, or humanized antibody, and fragments thereof, such as Fab, F(ab')$_2$, Fv, scFv (single chain antibody), or dAb (domain antibody; see Ward, et. Al., 1989, Nature, 341:544-546). "Monoclonal antibody" denotes a population of antibody molecules that contain only one type an antigen-binding site capable of immunoreacting with or binding to a particular antigen. Monoclonal antibodies can be derived from various species, e.g., mouse and human.

Preferably, the antibody used in this invention is an anti-IL-20 antibody 7E. The term "anti-IL-20 antibody 7E" refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent.

A "functional equivalent" of mAb 7E is an antibody that (1) specifically binds to human IL-20, and (2) contains a heavy chain variable region ($V_H$) at least 70% (e.g., 80%, 90%, or 95%) identical to that of mAb 7E (shown below as SEQ ID NO: 2, encoded by the nucleotide sequence of SEQ ID NO:1) and a light chain variable region ($V_L$) at least 70% (e.g., 80%, 90%, or 95%) identical to that of mAb 7E (shown below as SEQ ID NO: 4, encoded by the nucleotide sequence of SEQ ID NO:3). See U.S. patent application Ser. No. 11/763,812.

```
Nucleotide sequence (SEQ ID NO: 1) and amino acid sequence
(SEQ ID NO: 2) of mAb 7E heavy chain variable region
gaa ttg aag ctt gag gag tct gga gga ggc ttg gtg cag cct gga   45
 E   L   K   L   E   E   S   G   G   G   L   V   Q   P   G   15 gga tcc atg aaa ctc tct tgt gct gcc tct gga ttc act ttt agt    90
 G   S   M   K   L   S   C   A   A   S   G   F   T   F   S   30 gac gcc tgg atg gac tgg gtc cgc cag tct cca gag aag ggg ctt  135
 D   A   W   M   D   W   V   R   Q   S   P   E   K   G   L   45 gag tgg att gct gaa att aga agc aaa gct aat aat tat gca aca  180
 E   W   I   A   E   I   R   S   K   A   N   N   Y   A   T   60 tac ttt gct gag tct gtg aaa ggg agg ttc acc atc tca aga gat  215
 Y   F   A   E   S   V   K   G   R   F   T   I   S   R   D   75
```

-continued

| gat | tcc | aaa | agt | ggt | gtc | tac | ctg | caa | atg | aac | aac | tta | aga | gct | 270 |
| D | S | K | S | G | V | Y | L | Q | M | N | N | L | R | A | 90 |

| gag | gac | act | ggc | att | tat | ttc | tgt | acc | aag | tta | tca | cta | cgt | tac | 315 |
| E | D | T | G | I | Y | F | C | T | K | L | S | L | R | Y | 105 |

| tgg | ttc | ttc | gat | gtc | tgg | ggc | gca | ggg | acc | acg | gtc | acc | gtc | tcc | 360 |
| W | F | F | D | V | W | G | A | G | T | T | V | T | V | S | 120 |

| tca | | | | | | | | | | | | | | | 363 |
| S | | | | | | | | | | | | | | | 121 |

Nucleotide sequence (SEQ ID NO: 3) and amino acid sequence
(SEQ ID NO: 4) of mAb 7E light chain variable region

| gat | ttt | gtg | atg | acc | cag | act | cca | ctc | act | ttg | tcg | gtt | acc | att | 45 |
| D | F | V | M | T | Q | T | P | L | T | L | S | V | T | I | 15 |

| gga | caa | cca | gcc | tcc | atc | tct | tgc | aag | tca | agt | cag | agc | ctc | ttg | 90 |
| G | Q | P | A | S | I | S | C | K | S | S | Q | S | L | L | 30 |

| gat | agt | gat | gga | aag | aca | tat | ttg | aat | tgg | ttg | tta | cag | agg | cca | 135 |
| D | S | D | G | K | T | Y | L | N | W | L | L | Q | R | P | 45 |

| ggc | cag | tct | cca | aag | cac | ctc | atc | tat | ctg | gtg | tct | aaa | ctg | gac | 180 |
| G | Q | S | P | K | H | L | I | Y | L | V | S | K | L | D | 60 |

| tct | gga | gtc | cct | gac | agg | ttc | act | ggc | agt | gga | tca | ggg | acc | gat | 215 |
| S | G | V | P | D | R | F | T | G | S | G | S | G | T | D | 75 |

| ttc | aca | ctg | aga | atc | agc | aga | gtg | gag | gct | gag | gat | ttg | gga | gtt | 270 |
| F | T | L | R | I | S | R | V | E | A | E | D | L | G | V | 90 |

| tat | tat | tgc | tgg | caa | agt | aca | cat | ttt | ccg | tgg | acg | ttc | ggt | gga | 315 |
| Y | Y | C | W | Q | S | T | H | F | P | W | T | F | G | G | 105 |

| ggc | acc | aag | ctg | gaa | atc | aaa | cgg | | | | | | | | 339 |
| G | T | K | L | E | I | K | R | | | | | | | | 113 |

As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

A functional equivalent of mAb 7E can be its fragment generated by enzyme digestion, e.g., Fab or F(ab')$_2$. It also can be a genetically engineered antibody containing the $V_H$ and $V_L$ regions of mAb 7E. Examples of such antibodies include, but are not limited to, a single-chain antibody in which the $V_H$ and $V_L$ of mAb 7E are covalently fused via a linker (e.g., a peptide linker), and a mouse-human chimeric antibody, in which the $V_H$ and $V_L$ of mAb 7E are respectively linked with the constant regions of the heavy and light chains of a human IgG.

The functional equivalent can also be a humanized antibody. The term "humanized antibody" refers to a non-human antibody, in which the frame regions (FRs) of its $V_H$ and $V_L$ and the constant regions, if any, are replaced with FRs and the constant regions of a human antibody. Further, the mAb 7E functional equivalent can be generated by introducing mutations in the FRs of either $V_H$ or $V_L$. It is well known that complementarity-determining regions (CDRs) of an antibody determine its antigen specificity. Accordingly, mutations in FRs normally would not affect antibody specificity. The CDRs and FRs of an antibody can be determined based on the amino acid sequences of its $V_H$ and $V_L$. See www.bioinf.org.uk/abs. The binding-specificity of the functional equivalents described herein can be examined using methods known in the art, e.g., ELISA or western-blot analysis.

The anti-IL-20 antibody used in the method of this invention can be prepared via conventional methods. See, for example, Harlow and Lane, (1988) Antibodies: A Laboratory Manual, Cold Spring Harbor Laboratory, New York.

In general, to produce antibodies against a peptide, the peptide can be coupled to a carrier protein, such as KLH, mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production. In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

When used for treating stroke, the anti-IL-20 antibody described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

To practice the method provided in this application, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bio-availability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

In addition, the pharmaceutical composition described above can be administered to the subject via injectable depot routes of administration such as using 1-, 3-, or 6-month depot injectable or biodegradable materials and methods.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Overexpression of IL-20 in Rats Suffering from Ischemic Stroke

Ischemic stroke was induced in male Sprague-Dawley rats as follows. Rats (200 to 300 g) were obtained from the Laboratory Animal Center (National Cheng Kung University, Tainan, Taiwan) and fed with standard laboratory chow and drinking water (ad libitum). They were handled according to the guidelines set forth by the Council for International Organization of Medical Sciences on Animal Experimentation (World Health Organization, Geneva, Switzerland) and the guidelines set forth by National Cheng Kung University.

Transient focal cerebral ischemia was induced using intraluminal occlusion of the right middle cerebral artery (MCAO) in these rats. More specifically, the root of the right middle cerebral artery (MCA) was occluded by inserting a silicone-coated 4.0 nylon thread from the bifurcation of the internal and external carotid arteries. The tip of the thread was placed 18 mm distal to the bifurcation. The thermocouple needle probe was inserted into the temporal muscle to maintain the temperature at 37.0±0.1° C. with a heating lamp during surgery. For ischemic reperfusion, the cerebral blood flow was restored 90 minutes after MCAO was performed by pulling the thread for 5 mm. After the surgical incision was sutured, the rats were allowed to recover from anesthesia. The contralateral limbs of all the rats were paralyzed after they had recovered from anesthesia.

Three days after MCAO, rats were sacrificed and the brains were collected for lesion analysis. Brain sections (2-mm thick) were stained with 2% TTC (2,3,5-Triphenyltetrazolium chloride) (Sigma) at 37° C. for 30 minutes with gentle shaking and then fixed with 10% formalin in PBS. The stained slices were photographed, and the sizes of the infarcts were quantified using an imaging software (Adobe Photoshop 10). The brain tissues obtained from ischemic rats were also subjected to immunohistochemical staining to examine the expression levels of IL-20. Briefly, paraffin-embedded rat-brain sections were processed for immunohistochemistry staining using mAb 7E as described in Wei et al., Clin Immunol, 2005, 117:65-72; and Chen et al., Genes Immun. 2005, 6:493-499. Isotype-labeled mouse IgG, was used as a negative control. Immunoreactivity was detected using a 3-amino-9-ethylcarbazole (AEC) substrate kit for peroxidase (DAKO Corporation, Carpinteria, Calif.) and the nuclei were counterstained with Mayer's hematoxylin (ThermoShandon).

Results thus obtained showed that the levels of IL-20 in the ischemic hemisphere were significantly higher than those in the contralateral hemisphere of the control rats and the MCAO rats ($p<0.05$). See FIG. 1, panel A. The contralateral expression levels of IL-20 in the MCAO rats were not significantly different from those in both hemispheres of the control rats, indicating that IL-20 was upregulated only in ischemic-infarcted lesions. See FIG. 1, panel B.

Effect of Anti-IL-20 Monoclonal Antibody 7E in Treating Rats Suffering from Ischemic Stroke Ischemic rats, induced by the method described above, were treated with mAb 7E (10 mg/kg) or PBS as a negative control immediately after ischemic reperfusion by intravenous injection. In PBS-treated MACO rats, the median infarct area was 34.3 $mm^2$ (25th to 75th percentiles 36.8-31.5 $mm^2$). Surprisingly, the median infarct area in the mAb 7E-treated MACO rats was 26.4 $mm^2$ (25th to 75th percentiles 30.1-23.8 $mm^2$), much smaller than that in the PBS treated rats. These results, which were statistically significant ($p<0.05$), demonstrated that mAb 7E efficiently ameliorated infarction in the MACO rats. Furthermore, immunohistochemical staining analysis showed that the number of IL-20 positive, glia-like cells was reduced in mAb 7E-treated MCAO rats, compared to that in PBS-treated MCAO rats. In addition, results obtained from an ELISA assay using brain lyastes showed that mAb 7E reduced the protein levels of IL-20 and monocyte chemotactic protein-1 (MCP-1) ($p<0.05$), both of which were up-regulated in ischemic stroke. MCP-1 is a protein involved in cerebral injury.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating ischemic stroke, said method comprising identifying a subject who has ischemic stroke, and administering to the subject an antibody specific to IL-20, wherein the anti-IL-20 antibody contains a $V_H$ region including all the complementarity-determining regions in the $V_H$ region of mAb 7E and a $V_L$ region including all the complementarity-determining regions in the $V_L$ region of mAb 7E, wherein mAb 7E is produced by the hybridoma cell line deposited with the American Type Culture Collection as Deposit Number PTA-8687.

2. The method of claim 1, wherein the anti-IL-20 antibody is mAb 7E produced by the hybridoma cell line deposited with the American Type Culture Collection as Deposit Number PTA-8687.

3. The method of claim 1, wherein the anti-IL-20 antibody is a functional fragment of mAb 7E.

4. The method of claim 1, wherein the anti-IL-20 antibody is a Fab, a F(ab')$_2$, a single chain antibody or a chimeric antibody.

5. The method of claim 1, wherein the anti-IL-20 antibody is a humanized antibody.

6. The method of claim 1, wherein the antibody contains the $V_H$ and $V_L$ regions of mAb 7E.

* * * * *

SEQUENCE LISTING

<160> NUMBER OF SEQ ID NOS: 4

<210> SEQ ID NO 1
<211> LENGTH: 363
<212> TYPE: DNA
<213> ORGANISM: Artificial Sequence
<220> FEATURE:
<223> OTHER INFORMATION: Synthetic contruct
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 1

```
gaa ttg aag ctt gag gag tct gga gga ggc ttg gtg cag cct gga gga      48
Glu Leu Lys Leu Glu Glu Ser Gly Gly Gly Leu Val Gln Pro Gly Gly
1               5                   10                  15 tcc atg aaa ctc tct tgt gct gcc tct gga ttc act ttt agt gac gcc      96
Ser Met Lys Leu Ser Cys Ala Ala Ser Gly Phe Thr Phe Ser Asp Ala
            20                  25                  30 tgg atg gac tgg gtc cgc cag tct cca gag aag ggg ctt gag tgg att     144
Trp Met Asp Trp Val Arg Gln Ser Pro Glu Lys Gly Leu Glu Trp Ile
        35                  40                  45 gct gaa att aga agc aaa gct aat aat tat gca aca tac ttt gct gag     192
Ala Glu Ile Arg Ser Lys Ala Asn Asn Tyr Ala Thr Tyr Phe Ala Glu
    50                  55                  60
```

```
tct gtg aaa ggg agg ttc acc atc tca aga gat gat tcc aaa agt ggt    240
Ser Val Lys Gly Arg Phe Thr Ile Ser Arg Asp Asp Ser Lys Ser Gly
 65                  70                  75                  80 gtc tac ctg caa atg aac aac tta aga gct gag gac act ggc att tat    288
Val Tyr Leu Gln Met Asn Asn Leu Arg Ala Glu Asp Thr Gly Ile Tyr
                 85                  90                  95 ttc tgt acc aag tta tca cta cgt tac tgg ttc ttc gat gtc tgg ggc    336
Phe Cys Thr Lys Leu Ser Leu Arg Tyr Trp Phe Phe Asp Val Trp Gly
            100                 105                 110 gca ggg acc acg gtc acc gtc tcc tca                                363
Ala Gly Thr Thr Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu Lys Leu Glu Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                 20                  25                  30

Trp Met Asp Trp Val Arg Gln Ser Pro Glu Lys Gly Leu Glu Trp Ile
             35                  40                  45

Ala Glu Ile Arg Ser Lys Ala Asn Asn Tyr Ala Thr Tyr Phe Ala Glu
         50                  55                  60

Ser Val Lys Gly Arg Phe Thr Ile Ser Arg Asp Asp Ser Lys Ser Gly
 65                  70                  75                  80

Val Tyr Leu Gln Met Asn Asn Leu Arg Ala Glu Asp Thr Gly Ile Tyr
                 85                  90                  95

Phe Cys Thr Lys Leu Ser Leu Arg Tyr Trp Phe Phe Asp Val Trp Gly
            100                 105                 110

Ala Gly Thr Thr Val Thr Val Ser Ser
        115                 120

<210> SEQ ID NO 3
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 3 gat ttt gtg atg acc cag act cca ctc act ttg tcg gtt acc att gga     48
Asp Phe Val Met Thr Gln Thr Pro Leu Thr Leu Ser Val Thr Ile Gly
  1               5                  10                  15 caa cca gcc tcc atc tct tgc aag tca agt cag agc ctc ttg gat agt     96
Gln Pro Ala Ser Ile Ser Cys Lys Ser Ser Gln Ser Leu Leu Asp Ser
                 20                  25                  30 gat gga aag aca tat ttg aat tgg ttg tta cag agg cca ggc cag tct    144
Asp Gly Lys Thr Tyr Leu Asn Trp Leu Leu Gln Arg Pro Gly Gln Ser
             35                  40                  45 cca aag cac ctc atc tat ctg gtg tct aaa ctg gac tct gga gtc cct    192
Pro Lys His Leu Ile Tyr Leu Val Ser Lys Leu Asp Ser Gly Val Pro
         50                  55                  60
```

```
gac agg ttc act ggc agt gga tca ggg acc gat ttc aca ctg aga atc      240
Asp Arg Phe Thr Gly Ser Gly Ser Gly Thr Asp Phe Thr Leu Arg Ile
 65              70                  75                  80 agc aga gtg gag gct gag gat ttg gga gtt tat tat tgc tgg caa agt      288
Ser Arg Val Glu Ala Glu Asp Leu Gly Val Tyr Tyr Cys Trp Gln Ser
                 85                  90                  95 aca cat ttt ccg tgg acg ttc ggt gga ggc acc aag ctg gaa atc aaa      336
Thr His Phe Pro Trp Thr Phe Gly Gly Gly Thr Lys Leu Glu Ile Lys
                100                 105                 110 cgg                                                                  339
Arg

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Phe Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys His Leu Ile Tyr Leu Val Ser Lys Leu Asp Ser Gly Val Pro
         50                  55                  60

Asp Arg Phe Thr Gly Ser Gly Ser Gly Thr Asp Phe Thr Leu Arg Ile
 65              70                  75                  80

Ser Arg Val Glu Ala Glu Asp Leu Gly Val Tyr Tyr Cys Trp Gln Ser
                 85                  90                  95

Thr His Phe Pro Trp Thr Phe Gly Gly Gly Thr Lys Leu Glu Ile Lys
                100                 105                 110

Arg
```